(12) United States Patent
Van Bommel et al.

(10) Patent No.: US 10,345,238 B2
(45) Date of Patent: Jul. 9, 2019

(54) LIGHT SOURCE WITH ADAPTED SPECTAL OUTPUT

(71) Applicant: SIGNIFY HOLDING B.V., Eindhoven (NL)

(72) Inventors: Ties Van Bommel, Horst (NL); Rifat Ata Mustafa Hikmet, Eindhoven (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 14/888,798

(22) PCT Filed: Apr. 30, 2014

(86) PCT No.: PCT/EP2014/058810
§ 371 (c)(1),
(2) Date: Nov. 3, 2015

(87) PCT Pub. No.: WO2014/177607
PCT Pub. Date: Nov. 6, 2014

(65) Prior Publication Data
US 2016/0076736 A1 Mar. 17, 2016

(30) Foreign Application Priority Data
May 3, 2013 (EP) .................................. 13166395

(51) Int. Cl.
*A61B 5/00* (2006.01)
*G01N 21/64* (2006.01)
(Continued)

(52) U.S. Cl.
CPC ....... *G01N 21/6447* (2013.01); *A61B 5/0071* (2013.01); *F21K 9/64* (2016.08);
(Continued)

(58) Field of Classification Search
CPC ....... A61B 5/0071; F21V 9/16; F21V 14/006; F21V 14/08
See application file for complete search history.

(56) References Cited

U.S. PATENT DOCUMENTS

| 2004/0119086 A1 | 6/2004 | Yano et al. |
| 2008/0231162 A1* | 9/2008 | Kurihara ................. F21V 9/10 |
| | | 313/487 |

(Continued)

FOREIGN PATENT DOCUMENTS

| CN | 101802703 A | 8/2010 |
| CN | 102693971 A | 9/2012 |

(Continued)

OTHER PUBLICATIONS

Mieog et all. 2011. Toward Optimization of Imaging System and Lymphatic Tracer for Near-Infrared Fluorescent Sentinel Lymph Node Mapping in Breast Cancer. Annals of Surgical Oncology, vol. 18, pp. 2483-2491.*

(Continued)

*Primary Examiner* — Zheng Song
(74) *Attorney, Agent, or Firm* — Akarsh P. Belagodu

(57) ABSTRACT

The white light spotlight for luminescence (e.g. biomarker) detection according to the present application includes: at least one solid state light emitting element to emit primary light, and a plurality of wavelength converting materials, to convert part of primary light into secondary light, provided as an array of independent wavelength converting domains, wherein different domains comprise converting materials producing different secondary light emission bands/peaks, each converting material being adapted to convert primary light into secondary light, wherein each converting material is adapted to contribute to the total emission spectrum with at least one emission band/peak and the total secondary light emission provided by said converting materials provides a (Continued)

broad band emission spectrum except for at least one defined narrow wavelength range in which the spotlight produces no or significantly reduced light emission, and wherein the combined light emission from the converting materials is controllable to form said spectrum.

12 Claims, 6 Drawing Sheets

(51) Int. Cl.
    *F21V 21/084*     (2006.01)
    *H01L 25/075*     (2006.01)
    *F21L 4/00*     (2006.01)
    *F21K 9/64*     (2016.01)
    *F21V 9/30*     (2018.01)
    *H05B 33/08*     (2006.01)
    *F21L 4/02*     (2006.01)
    *H01L 33/50*     (2010.01)
    *F21W 131/205*     (2006.01)
    *F21Y 115/10*     (2016.01)

(52) U.S. Cl.
    CPC ............... *F21L 4/005* (2013.01); *F21V 9/30* (2018.02); *F21V 21/084* (2013.01); *G01N 21/6428* (2013.01); *G01N 21/6486* (2013.01); *H01L 25/0753* (2013.01); *H05B 33/0872* (2013.01); *F21L 4/027* (2013.01); *F21W 2131/205* (2013.01); *F21Y 2115/10* (2016.08); *G01N 2021/6439* (2013.01); *G01N 2021/6471* (2013.01); *G01N 2201/062* (2013.01); *G01N 2201/068* (2013.01); *H01L 33/504* (2013.01); *H01L 33/508* (2013.01); *H01L 2924/0002* (2013.01)

(56) References Cited

U.S. PATENT DOCUMENTS

| | | | |
|---|---|---|---|
| 2008/0246017 A1 | 10/2008 | Gillies et al. | |
| 2010/0002422 A1 | 1/2010 | Ho | |
| 2010/0254115 A1* | 10/2010 | Wegh | F21S 10/02 362/84 |
| 2010/0262017 A1 | 10/2010 | Frangioni | |
| 2011/0082369 A1 | 4/2011 | Mohr et al. | |
| 2011/0160541 A1 | 6/2011 | Koyama et al. | |
| 2011/0176091 A1* | 7/2011 | Boonekamp | C09K 11/0883 349/86 |
| 2011/0261561 A1 | 10/2011 | Gardner et al. | |
| 2012/0074833 A1* | 3/2012 | Yuan | H05B 33/14 313/483 |
| 2012/0300432 A1 | 11/2012 | Matsubayashi et al. | |
| 2013/0001597 A1* | 1/2013 | Anc | H01L 33/504 257/88 |
| 2013/0070443 A1* | 3/2013 | Pan | C09K 9/02 362/84 |
| 2013/0105854 A1 | 5/2013 | Jang et al. | |
| 2014/0111985 A1* | 4/2014 | Harbers | F21V 9/16 362/231 |
| 2014/0160728 A1* | 6/2014 | Kim | H01L 25/0753 362/84 |
| 2014/0267773 A1* | 9/2014 | Jeung | F21V 9/16 348/169 |
| 2015/0083932 A1* | 3/2015 | Rizo | A61B 5/0071 250/458.1 |
| 2015/0345746 A1* | 12/2015 | Fornasiero | F21V 9/16 362/231 |

FOREIGN PATENT DOCUMENTS

| | | |
|---|---|---|
| EP | 1568936 A1 | 8/2005 |
| JP | 2005237973 A | 9/2005 |
| JP | 2008034209 A | 2/2008 |
| JP | 2011146723 A | 7/2011 |
| JP | 2011233269 A | 11/2011 |
| RU | 2009144533 A | 6/2011 |
| RU | 2475887 C1 | 2/2013 |
| WO | WO2009050693 A1 | 4/2009 |
| WO | WO2011147521 A1 | 12/2011 |
| WO | 2013038579 A1 | 3/2013 |
| WO | 2013150455 A1 | 10/2013 |

OTHER PUBLICATIONS

Lawrence D. True et al; "Quantun Dots for Molecular Pathology, Their Time AHS Arrived", Journal of Molecular Diagnostics, vol. 9, No. 1, Feb. 2007, pp. 7-11.

\* cited by examiner

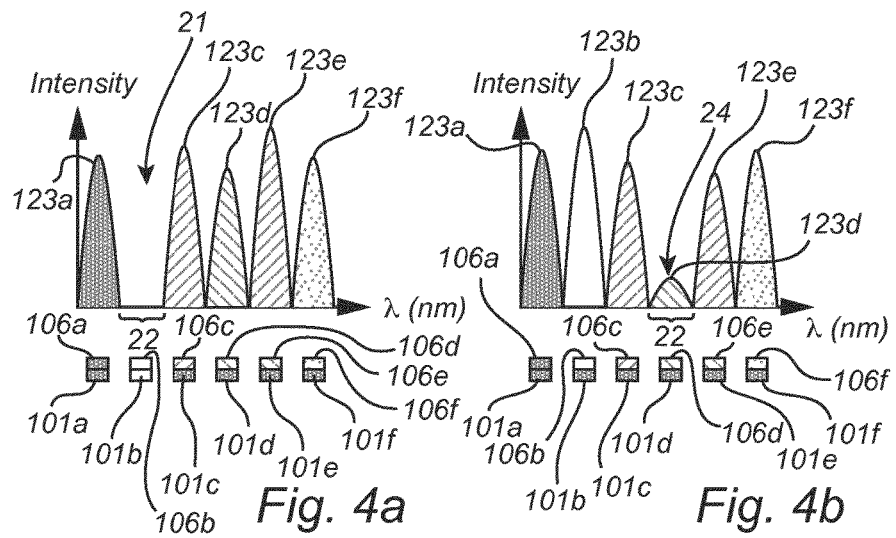
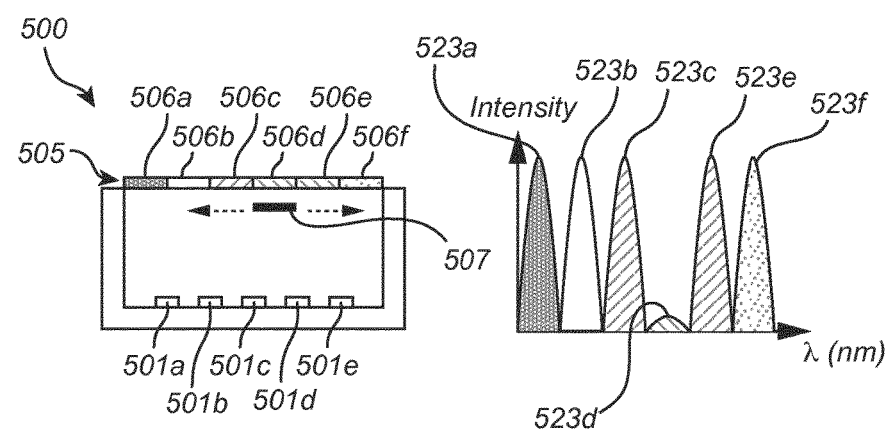
Fig. 4a    Fig. 4b    Fig. 5a    Fig. 5b

LIGHT SOURCE WITH ADAPTED SPECTAL OUTPUT

CROSS-REFERENCE TO PRIOR APPLICATIONS

This application is the U.S. National Phase application under 35 U.S.C. § 371 of International Application No. PCT/EP2014/058810, filed on Apr. 30, 2014, which claims the benefit of European Patent Application No. 13166395.7, filed on May. 3, 2013. These applications are hereby incorporated by reference herein.

FIELD OF THE INVENTION

The present invention relates to solid state light-emitting arrangements, devices and lighting systems utilizing wavelength converting materials for providing a desirable spectral output.

BACKGROUND OF THE INVENTION

Fluorescent biomarkers (biological markers) are fluorescent molecules that can be used for detecting a biological state or process, such as a pathogenic state or process or a particular cell or tissue type. Fluorescent biomarkers can for example be used for detecting diseases such as cancer. The fluorescent molecules can be injected into a patient or a biological sample and accumulate at the cancerous site. When irradiated with excitation light, the fluorescent molecules produce light emission of a predefined wavelength. Thus, cancerous tissue can be localized by localization of the fluorescent signal. However, the fluorescent signal can be difficult to detect, especially in a surgical environment which requires strong lighting.

US 2011/0082369 discloses an apparatus for displaying medical images during minimally invasive surgery. The apparatus is aimed at improving the clinical utility of the simultaneous display of a white light image of tissue and an enhanced image of tissue which has been made imageable e.g. by injection with fluorescing or emitting biomarker. The apparatus comprises a display device which displays a desaturated image of tissue and a color enhanced image combined with the desaturated image. The relative brightness between the desaturated image and the color enhanced image is set to provide improved information content.

However, there remains a need in the art for improved means of detecting fluorescent molecules, especially fluorescent biomarkers, not least in surgical environments.

SUMMARY OF THE INVENTION

It is an object of the present invention to overcome this problem, and to provide a light source, in particular a spotlight, having an emission spectrum that is adapted to facilitate detection of a fluorescent molecule.

According to a first aspect of the invention, this and other objects are achieved by a spotlight adapted to produce white light, comprising:
  at least one solid state light emitting element adapted to emit primary light, and
  a plurality of wavelength converting materials, adapted to convert part of the primary light into secondary light, provided as an array of independent wavelength converting domains, wherein different wavelength converting domains comprise wavelength converting materials producing different secondary light emission bands or peaks, each wavelength converting material being adapted to convert primary light into a secondary light wavelength range wherein the total secondary light emission provided by said wavelength converting materials provides a broad band emission spectrum except for at least one defined narrow wavelength range in which the spotlight produces no or significantly reduced light emission, and wherein the combined emission of light converted by the wavelength converting materials is controllable to form an emission spectrum with no or significantly reduced light emission in said at least one defined narrow wavelength range.

By "spotlight" is meant an artificial source of light producing a relatively focused light beam for illuminating a defined or limited area (as opposed to a lamp or luminaire for general illumination).

As used herein, the term "wavelength band" refers to a wavelength range, given in nanometers (nm), of the electromagnetic spectrum. "Wavelength band" and "wavelength range" may be used interchangeably.

As used herein, "emission band" refers to a wavelength range, or wavelength band of light that is emitted, e.g. by a light emitting element or a luminescent material. An emission band often includes an emission peak, with an intensity maximum somewhere within the emission band, and with lower emission towards the endpoints of the range. In the context of the present invention, "broad band emission" typically refers to emission bands with an emission peak having a full width at half maximum (FWHM) of more than 50 nm. Hence, "broad band emission spectrum" refers to an emission spectrum including such an emission peak.

Furthermore, "narrow band emission", "narrow emission band" refers to emission bands with an emission peak having a full width at half maximum (FWHM) of 50 nm or less.

"Narrow wavelength range" in the context of a wavelength band in which there is no or only low light emission typically refers to wavelength ranges having a span of 100 nm or less, such as 60 nm or less, e.g. 50 nm or less.

In the context of the present invention, the light emitted by a solid state light emitting element is referred to as "primary light" or sometimes as "pump light", and is usually intended to be at least partly converted by a luminescent material. Primary light may be visible light, e.g. blue or violet light, or may be UV light.

Light emitted by a luminescent material (wavelength converting material) by conversion of primary light may be referred to as "secondary light" or "converted light". This light is typically visible light.

The spotlight according to the invention is particularly suitable for illumination of an object generating a fluorescent or luminescent signal that is to be detected. The emission spectrum of the spotlight may be adapted to facilitate detection of any fluorescent or luminescent signal. The spotlight may emits full spectrum white light, except for a spectral "hole", positioned at a wavelength band which may correspond to the emission of a fluorescent molecule (marker). By "corresponds" is here meant that the wavelength band of the "hole" and the wavelength band of the fluorescent signal are the same or substantially the same, or at least partly overlapping.

Since the spotlight produces generally white light, preferably having a color point on or near the black body line as represented in the CIE chromaticity diagram, it provides general illumination of high quality for many application, including surgery.

The spotlight comprises a plurality of wavelength converting materials, each adapted to convert primary light into a secondary light wavelength range, wherein each wavelength converting material is adapted to contribute to the total emission spectrum with at least one emission band or peak, and wherein the combined emission of light converted by the wavelength converting materials is controllable to form an emission spectrum with no or significantly reduced light emission in said at least one defined narrow wavelength range. Hence, the total emission spectrum can be controlled to facilitate detection of a particular fluorescent or luminescent signal.

In particular, the spotlight comprises an array of independent wavelength converting domains, wherein different wavelength converting domains comprise wavelength converting materials producing different secondary light emission bands or peaks. Such wavelength converting domains may be independently controllable, e.g. via a respective pump LED element or via a shielding member. In some embodiments, the spotlight may further comprise a shielding member arranged to shield at least one wavelength converting domain from receiving primary light. The shielding member may be controllable to shield different wavelength converting domains. Alternatively, or additionally, the spotlight may comprise a plurality of independently controllable solid state light sources (light emitting elements), wherein each wavelength converting domain is arranged to receive light emitted by one of said independently controllable solid state light sources. The at least one wavelength converting material may comprise one or several types of quantum dots. Alternatively or additionally, the least one wavelength converting material comprise one or several types of organic wavelength converting materials. Both quantum dots and organic wavelength converting materials are advantageous since they produce narrow emission bands, and can be combined with other types of quantum dots and/or organic wavelength converting material to produce full spectrum white light.

In embodiments of the invention, the spotlight further comprises a light sensor and a control unit operatively connected to the light sensor and to said controllable shielding member and/or said independently controllable light sources, wherein said control unit is adapted to control the emission spectrum of the spotlight. Thus, the spotlight may be adapted to automatically control the intensity spectrum of the emitted light in response to a fluorescent or luminescent signal detected by the light sensor.

The spotlight according to the first aspect of the invention is particularly useful in medical or laboratory environments where detection of fluorescent markers is performed, e.g. during surgery, or during examination of patients or of biological samples.

Thus, in another aspect, the invention provides a torch comprising a spotlight as described herein. The torch light may be a head torch or a handheld torch.

In another aspect, the invention provides a surgical lighting system comprising at least one spotlight as described herein.

By "surgical light source" is meant a light source, such as a spotlight, intended for use in surgical or hospital environments, for illumination e.g. during surgery or medical examination. By "surgical lighting system" is meant a lighting apparatus comprising at least one surgical light source, fittings and a supporting structure e.g. for mounting in a ceiling or on a wall, and optionally comprising optical components such as reflectors, lenses etc.

In yet another aspect, the invention provides the use of a spotlight as described herein for illuminating an object comprising a fluorescent molecule. In some embodiments, the fluorescent molecule emits light in a wavelength range corresponding to a wavelength range in which the spotlight produces no or low intensity light emission. In some embodiments, the spotlight produces an emission spectrum comprising an emission peak in a wavelength range where the fluorescent molecule has an absorption peak; hence the emission from the spotlight may provide primary light for conversion by the fluorescent molecule and thus enhance the fluorescent signal.

In a further aspect the invention provides a method of detecting a fluorescent molecule, comprising illuminating an object comprising the fluorescent molecule using a spotlight as described herein. In embodiments of the invention, the fluorescent molecule may be a biomarker and the illuminated object may be a biological material.

Finally, in a further aspect, the invention provides a method of operating a spotlight comprising a light emitting arrangement, a light sensor and a control unit operatively connected to the light sensor and to a controllable shielding member and/or independently controllable light sources, the method comprising:

detecting light emitted by an object to be illuminated by the spotlight, typically using the light sensor;

controlling the operation at least one solid state light emitting element or a shielding member, respectively, to prevent or reduce emission of light of a wavelength range emitted by the object to be illuminated; and illuminating the object with light emitted by the spotlight.

Typically, the step of controlling the operation of the at least one solid state light emitting element is performed at least partly by the control unit.

It is noted that the invention relates to all possible combinations of features recited in the claims.

BRIEF DESCRIPTION OF THE DRAWINGS

This and other aspects of the present invention will now be described in more detail, with reference to the appended drawings showing embodiment(s) of the invention.

FIG. 1b is a graph showing the emission spectrum of a fluorescent molecule that may be detected using a light source having a spectrum as shown in FIG. 1a.

FIG. 4a schematically shows a plurality of light emitting elements and wavelength converting material as used in embodiments of the invention, and the resulting emission spectrum.

FIG. 4b schematically shows a plurality of light emitting elements and wavelength converting materials as used in other embodiments of the invention, and a resulting emission spectrum.

FIG. 5a is a side view of a light emitting arrangement including a shielding member as used in embodiments of the invention.

FIG. 5b is a graph illustrating an exemplary emission spectrum of a light emitting arrangement as shown in FIG. 5a.

FIG. 7b is a graph showing an exemplary emission spectrum of a light emitting arrangement as shown in FIG. 7a.

As illustrated in the figures, the sizes of layers and regions are exaggerated for illustrative purposes and, thus, are provided to illustrate the general structures of embodiments of the present invention. Like reference numerals refer to like elements throughout.

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled person.

The present inventors have realized that during the examination of a tissue injected with a fluorescent biomarker during surgery, the surgical light can overlap with the emission from the marker, which makes the fluorescence from the biomarker difficult to discern. The inventors have found that the use of a light source, typically a spotlight, having a "hole" or "dip" in the emission intensity spectrum at a wavelength band which corresponds to the emission of the fluorescent marker molecule can increase the detectability of the marker, while still providing the white light required for good visibility e.g. for a surgical procedure. The proposed light source can be provided using one or more solid state light emitting elements such as light emitting diodes (LEDs) and one or more wavelength converting materials (phosphors), possibly in combination with a wavelength blocking or absorbing member. Additionally, the inventors have found that light source which produces a spectral peak which corresponds to the absorption of the marker may further increase detectability of the marker.

Fluorescent labeling involves covalently attaching a fluorophore to a target molecule, such as a protein or a nucleic acid. This is generally accomplished using a reactive derivative of the fluorophore that selectively binds to a functional group of the target molecule. The target molecule may be used as a probe for detection of a target in a biological sample or in the body of a patient.

Reactive fluorescent dyes are available from many sources and can be obtained with different reactive groups for attachment to various functional groups within the target molecule. Common reactive groups include:

Derivatives of fluorescein and rhodamine such as FITC and TRITC; reactive towards primary amines to form a thioureido linkage between the compound of interest and the dye.

Succinimidyl esters such as NHS-fluorescein; reactive towards amino groups to form an amido bond.

Maleimide activated fluorophores such as fluorescein-5-maleimide; readily react with sulfhydryl groups. The sulfhydryl group adds to the double bond of the maleimide.

Additionally, quantum dots can also be used as fluorescent markers. In embodiments of the invention, any known type of fluorescent marker may be used.

Figure 1A:
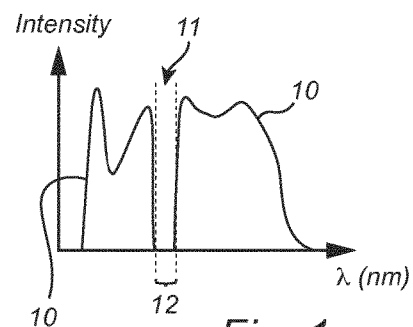
FIG. 1a is a graph illustrating an exemplary emission intensity spectrum of a light source according to embodiments of the invention.
Figure 1B:
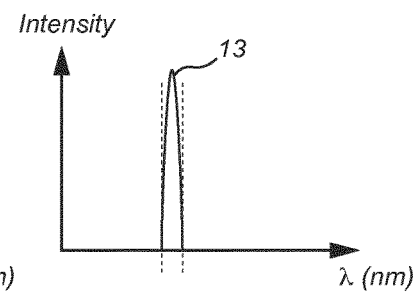

FIG. 1a is a graph illustrating an exemplary emission intensity spectrum of a light source according to embodiments of the invention. The light source, which is typically a spotlight, emits full spectrum white light 10, except for a spectral "hole" 11. The spectral "hole" 11 is positioned at a wavelength range 12 which corresponds to the emission 13 of a fluorescent molecule, schematically shown in FIG. 1b. By "corresponds" is here meant that the wavelength range 12 of the "hole" 11 and the wavelength range of the emission 13 are the same or substantially the same, or at least partly overlapping.

Figure 2:
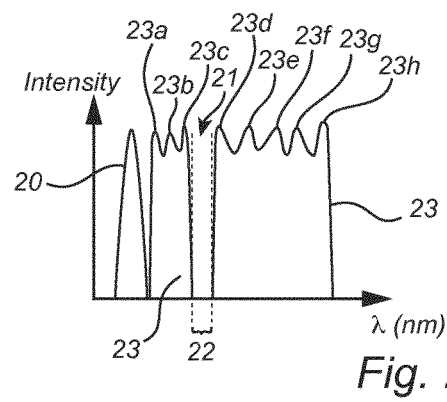
FIG. 2 shows another exemplary emission spectrum of a light source according to embodiments of the invention.

The emission spectrum of the light source may be obtained for example by the use of a blue or UV emitting solid state light emitting element, typically at least one LED element, and one or more wavelength converting materials. FIG. 2 shows another exemplary emission spectrum of a light source according to embodiments of the invention, which uses at least one blue LED element and a plurality of wavelength converting materials, e.g. quantum dots and/or organic phosphors. The at least one LED element provides blue light emission 20, and the wavelength converting materials (which use part of the blue light emitted by the LED for conversion) provide secondary light emission peaks 23a, 23b, 23c, 23d, 23e, 23f, 23g, 23h. Adjacent emission bands of the wavelength converting materials may partially overlap, so that the resulting spectrum is continuous over a wavelength range that is broader than the emission band of a single wavelength converting material. Also, the emission from the LED element may partially overlap an emission band of the secondary emission, e.g. the peak 23a. The emission 23 from the wavelength converting materials in combination with the emission 20 from the LED element spans the visible wavelength range, thus providing white light, except for a defined wavelength range 22 in which there is no emission, thus forming a "hole" 21 in the emission spectrum. The hole typically corresponds to the emission of a fluorescent molecule to be detected using the light source.

In some embodiments, to be described in more detail below, there may be some low intensity emission in the wavelength band corresponding to the emission of a fluorescent marker molecule to be detected, however in such embodiments the emission intensity of that emission band is considerably lower (e.g. having an intensity peak that represents 50% or less, such as 30% or less, for example 10% or less) than the average intensity of the rest of the spectrum emitted by the light source.

There are various ways of achieving the above emission spectra 10, 23 including the "hole" 11, 21.

Figure 3:
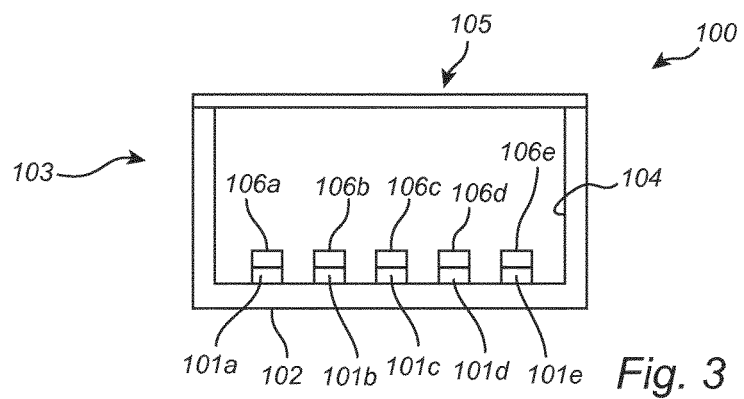
FIG. 3 is a side view of a light emitting arrangement used in embodiments of the invention.

In embodiments of the invention, a spectrum similar to that shown in FIG. 2 may be obtained by the use of at least one solid state light emitting element, here an LED element, and a plurality of wavelength converting materials. FIG. 3 shows a light emitting arrangement 100 used in embodiments of the invention, comprising plurality of LED elements 101a-e arranged on a bottom portion 102 of a reflective light mixing chamber 103 comprising a least one reflective side wall 104 (e.g. a cylindrical side wall) and a light exit window 105. Each LED element 101a-e is provided with a respective wavelength converting material 106a-e, here forming a plurality of phosphor-converted LEDs. It is however envisaged that the wavelength converting material need not be arranged directly on top of the respective LED element as is the case in FIG. 3, but may be provided at a more remote location in relation to the LED elements. Each LED element and its respective wavelength converting material may also be provided in a separate reflective chamber, cup, compartment or the like to reduce cross-talk between adjacent LEDs. In some embodiments, one or more LED elements may be used and the wavelength converting materials 106a-e may be provided at a remote location from the LED element(s), e.g. in the light exit window 105, such the light emitted by a particular LED element may be received by more than one wavelength converting material.

The LED element(s) may emit for example blue light, or UV light. If UV emitting LED elements are used, a blue wavelength converting material may be used for converting part of the UV light into blue light, and the other wavelength converting materials are typically adapted for conversion of UV light into the respective secondary light wavelength ranges. If a blue emitting LED element is used, a blue wavelength converting material may be omitted.

Each type of wavelength converting material 106a-e provides a separate emission band (typically including an emission peak) that may contribute to the total output spectrum, which is typically perceived as white light. As an example, in one embodiment, a blue LED is used in combination with a yellow wavelength converting, an orange wavelength converting material, an orange-red wavelength converting material and a darker red wavelength converting material. However, the light emitting arrangement may lack a green wavelength converting material, so that no emission in the green part of the spectrum is produced, hence forming a "hole" in the spectrum.

As shown in FIG. 3, in embodiments of the invention the light emitting arrangement may comprise a plurality of phosphor-converted LEDs in which one LED is associated with and pumps a particular wavelength converting material. In such embodiments, the wavelength converting materials 106a-e may together represent the entire visible spectrum (possibly with the exception of blue, which can be provided by the primary light of the LED element), i.e., the light source need not lack a particular wavelength converting material in order to produce a "hole" in the total emission spectrum. Instead, as schematically shown in FIG. 4a, an LED element 101b associated with a wavelength converting material 106b emitting light of a wavelength range corresponding to the emission of a fluorescent molecule to be detected may simply be switched off. Alternatively, as schematically shown in FIG. 4b, an LED element 101d may be controlled to produce low intensity light emission compared to the emission of the other phosphor-converted LEDs, so that the emission of the associated wavelength converting material 106d is significantly reduced, forming a "dip" in the total emission spectrum.

The LED elements may be independently controllable.

It is noted that the spectral "hole" or "dip" may represent any desirable wavelength range, corresponding to the emission of any fluorescent molecule.

In another embodiment of the invention, shown in FIG. 5a, a light emitting arrangement 500 comprises a plurality of LED elements 501a-e, typically blue LED elements, arranged within a light mixing chamber similar to that described above with reference to FIG. 3. In this embodiment, a plurality of wavelength converting domains 506a-f are provided in a light exit window 505 to receive light from the LED elements, each wavelength converting domain comprising a particular type of wavelength converting material. It is noted that the number of wavelength converting materials and/or wavelength converting domains need not be the same as the number of LED elements. In fact, it may be possible to use a single LED element instead of the plurality of LED elements 501a-e.

Further, a shielding member 507 is provided in the path of light from the LED elements 501a-e to the light exit window to prevent light from the LED elements from reaching at least one wavelength converting domain, here wavelength converting domain 506d. The shielding member 507 may have dimensions similar or identical to the dimensions of a wavelength converting domain. FIG. 5b shows an exemplary emission spectrum that can be obtained by shielding the wavelength converting domain 506d.

As can be understood by comparing the spectra shown in FIGS. 4a-b and 5b, a similar or identical emission spectrum can be obtained by different means, here down-regulating or switching off a particular LED element, or partially or completely shielding a particular wavelength converting material from receiving primary light.

In some embodiments, the shielding member 507 is moveable between different positions in the plane between the LED element(s) and the wavelength converting domains, such that it may be controlled to shield any one of the wavelength converting domains 505a-f. The shielding member may be mechanically or electrically controllable, e.g. by a user of the light source.

Figure 6A:
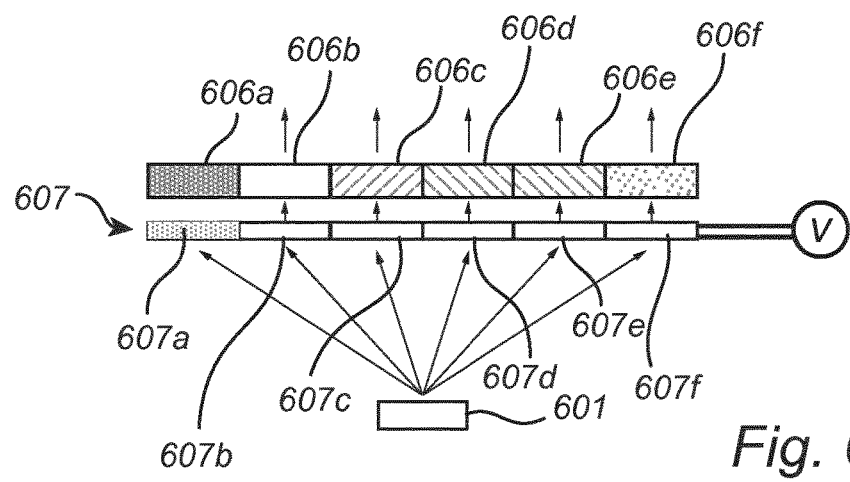
FIGS. 6a-b are a schematic side views of a light emitting arrangement comprising an electrically controllable shielding member as used in embodiments of the invention.
Figure 6B:
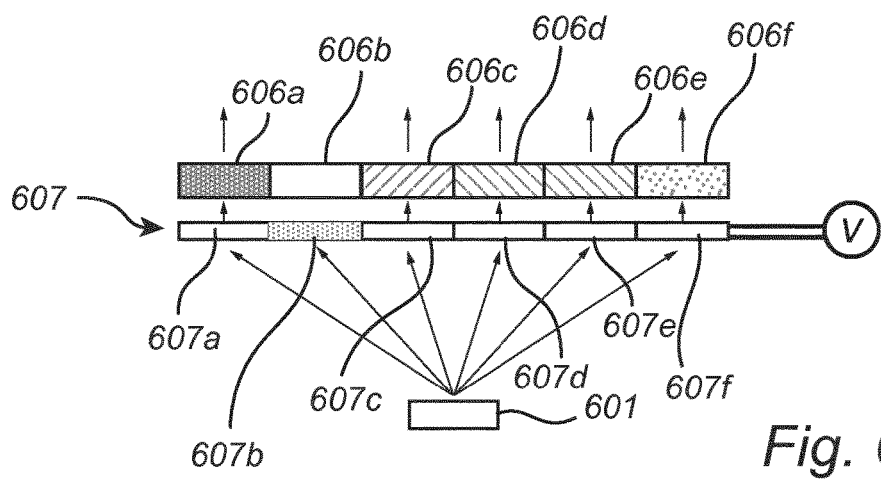

In one embodiment, control of a shielding effect may be achieved by electrical means. For example, the shielding member may comprise an electrically controllable layer comprising a plurality of independently controllable shielding domains, each domain being arranged to be capable of shielding a wavelength converting domain. The electrically controllable layer may for example comprise an electro-optical device whose optical properties (in particular light transmission) may be controlled by the application of an electric potential. FIGS. 6a-b illustrate an example of such a shielding member 607 in the form of an electrically controllable layer, comprising a plurality of independently controllable shielding domains 607a-f, arranged in the path of light between a light source 601 and wavelength converting domains 606a-f. Each shielding domain 607a-f may be reversibly switchable between a light transmissive state (e.g. domain 607b-f of FIG. 6a, and domains 607a and 607c-f of FIG. 6b) where light (indicated by arrows) can be received by a corresponding wavelength converting domain located behind said shielding domain as seen from a solid-state light emitting element 601, and a light blocking or shielding state (domain 607a of FIG. 6a, and domain 607b of FIG. 6b), in which the shielding domain is non-transmissive and thus blocks light from reaching the corresponding wavelength converting domain. Examples of suitable electrically controllable devices include liquid crystal devices, such as polymer dispersed liquid crystal (PDLC) devices or liquid crystal gel devices, in-plane switching electrophoretic devices, electrochromic devices and electrowetting devices.

Figure 7A:
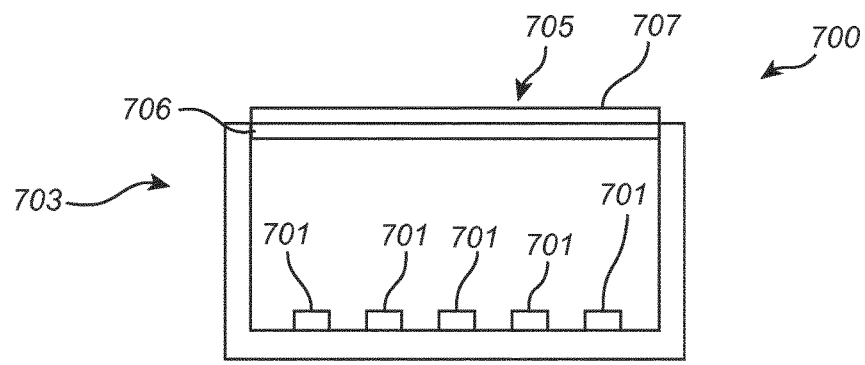
FIG. 7a is a side view of a light emitting arrangement comprising a wavelength-specific filter or absorbing material.
Figure 7B:
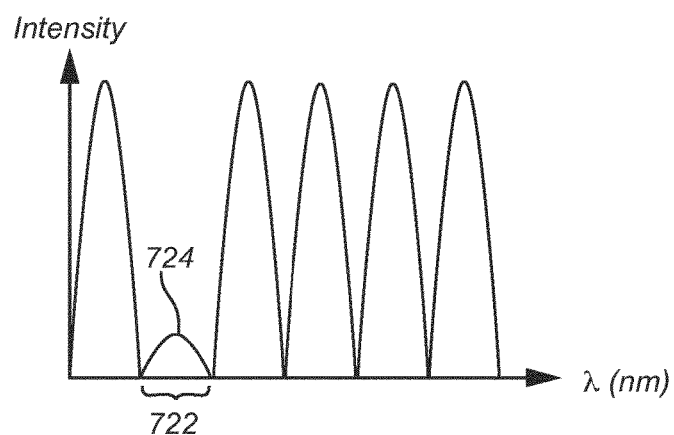

FIG. 7a-b illustrates a light source comprising one or more wavelength converting materials in combination with a wavelength-specific filter or absorbing material. In one embodiment, a light emitting arrangement 700 comprises one or more LED elements 701 arranged in a reflective chamber 703 optionally similar to that described with reference to FIG. 3, and at least one wavelength converting material 706 arranged in a light exit window 705 to receive light emitted by the LED elements 701. The wavelength converting material 706 may be a single wavelength converting material providing broad band emission, or may be composed of a plurality of different narrow band emitting wavelength converting materials which together provide broad band emission, such that the combined emission of the LED elements and the wavelength converting material(s) may be perceived as white.

Further, on a light output side of the wavelength converting material 706 (i.e., downstream of the wavelength converting material 706 as seen in the path of light from the LED elements 701a-e), a wavelength-specific filter 707 is provided which may absorb and/or reflect light of a specific wavelength range, corresponding to the wavelength range in which reduced or no emission is desired, for example green light. Other wavelengths are typically transmitted. An exemplary resulting emission spectrum, having an intensity dip at an emission band representing green light, is shown in FIG. 7b. It is possible that the wavelength-specific filter 707 may completely block the transmission of a particular wavelength range, to produce a "hole" in the emission spectrum.

In embodiments of the invention, the emission spectrum of the light source may comprise an intensity peak in a wavelength range in which a fluorescent molecule has an absorption peak. Hence, by supplying additional excitation light, the light source may enhance the fluorescent signal from a marker molecule illuminated with the light source, which may further increase detectability of the marker molecule. An intensity peak may be achieved e.g. by using additional light emitting elements and/or wavelength converting materials supplying the relevant emission band, or by controlling a phosphor-converted light emitting element supplying the relevant emission band to emit light of increased intensity relative to at other light emitting elements of the light source.

In embodiments of the invention, the emission spectrum emitted by the light source may be controllable depending on the fluorescent molecule to be detected. For example, the emission spectrum may be adapted by manually adjusting the light source to produce light having a spectral hole at a desired position, e.g. a predetermined wavelength range which may be one out of several possible pre-determined wavelength ranges. In such embodiments, the light source typically comprises an adjustment member that is operable by a user of the light source, and a control device operatively connecting the adjustment member and relevant part(s) of the light emitting arrangement, e.g. one or more LED element(s) and/or a shielding member.

Figure 8:
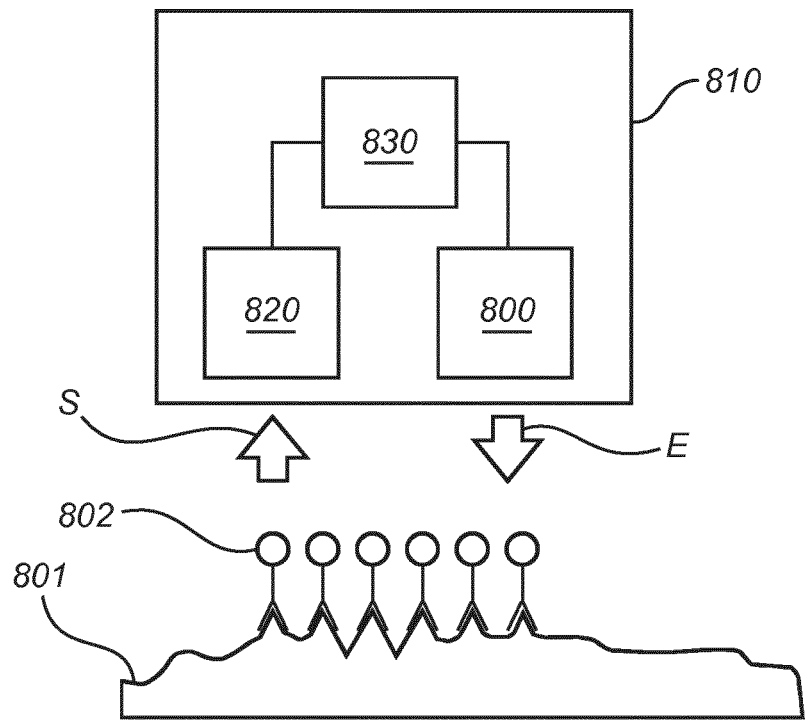
FIG. 8 schematically represents the components of a light source including a light sensor for detecting light emitted by a fluorescent molecule, a control unit, and a light emitting arrangement, according to embodiments of the invention.

Alternatively, as illustrated in FIG. 8, a light source 810 according to embodiments of the invention may be adapted to automatically control the intensity spectrum of the emitted light E in response to a fluorescent signal S from an object 801 comprising a fluorescent molecule 802. In such embodiments, the light source 810 may comprise a light emitting arrangement 800 which may be as described above with reference to any of FIGS. 3-7, a light sensor 820 for detecting the fluorescent signal S, and a control unit 830 for receiving information from the light sensor 820 about the fluorescent signal, the control unit being operatively connected to relevant part(s) of the light emitting arrangement 800 to control, for instance, the operation of LED element(s) and/or a shielding member, so as to produce an output emission spectrum E with no or reduced emission in the wavelength range corresponding to the detected fluorescent signal S.

Figure 9:
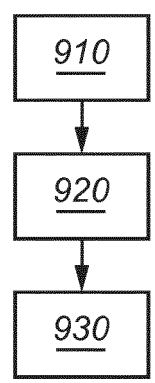
FIG. 9 is a block diagram representing a method of operating a light source according to embodiments of the invention.

FIG. 9 is a block diagram schematically illustrating a method of operating a light source, e.g. a spotlight, according to embodiments of the invention. The method comprises a step 910 of detecting light emitted by an object comprising a fluorescent molecule. The object is intended to be illuminated with the light source. The step 910 may be carried out by a light sensor as described above, or by a user by visual inspection of the object. A step 920 comprises controlling the operation of at least one solid state light emitting element of the light source and/or controlling the operation of a shielding member, to partially or completely prevent or reduce emission of light of the wavelength range that is emitted by the fluorescent molecule, so as to produce an adapted emission spectrum with a "hole" or "dip" at the required position. A step 930 comprises illuminating the object using the light source producing said adapted emission spectrum.

In embodiments of the invention the wavelength converting material(s) may comprise one or more inorganic phosphor(s), one or more organic phosphor(s), and/or quantum dots.

Examples of inorganic wavelength converting materials may include, but are not limited to, cerium (Ce) doped YAG ($Y_3Al_5O_{12}$) or LuAG ($Lu_3Al_5O_{12}$). Ce doped YAG emits yellowish light, whereas Ce doped LuAG emits yellow-greenish light. Examples of other inorganic phosphors materials which emit red light may include, but are not limited to ECAS ($Ca_{1-x}AlSiN_3:Eu_x$ wherein $0<x\leq1$; preferably $0<x\leq0.2$) and BSSN ($Ba_{2-x-z}M_xSi_{5-y}Al_yN_{8-y}O_y:Eu_z$ wherein M represents Sr or Ca, $0\leq x\leq1$, $0\leq y\leq4$, and $0.0005\leq z\leq0.05$, preferably $0\leq x\leq0.2$). One or more inorganic material may be used as the sole wavelength converting material(s), or may be combined with one or more organic phosphor(s) and/or quantum dots.

Organic phosphors are advantageous in that the bandwidth and the position of the emission spectrum in the visible wavelength range can be readily designed as desired by choosing a specific molecular structure emitting light of a desired wavelength distribution. By combining organic phosphor molecules with different emission characteristics, an emission spectrum with a desired spectral "hole" can be obtained. Any suitable combination of organic wavelength converting materials, optionally with inorganic phosphor material(s) and/or quantum dots, may be used in the present invention. Examples of organic wavelength converting materials that may be used include organic luminescent materials based on perylene derivatives, for example compounds sold under the name Lumogen® by BASF. Examples of suitable compounds include, but are not limited to, Lumogen® Red F305, Lumogen® Orange F240, Lumogen® Yellow F083, and Lumogen® F170.

Quantum dots are small crystals of semiconducting material generally having a width or diameter of only a few nanometers. When excited by incident light, a quantum dot emits light of a color determined by the size and material of the crystal. Light of a particular color can therefore be produced by adapting the size of the dots. Most known quantum dots with emission in the visible range are based on cadmium selenide (CdSe) with a shell such as cadmium sulfide (CdS) and zinc sulfide (ZnS). Cadmium free quantum dots such as indium phosphode (InP), and copper indium sulfide ($CuInS_2$) and/or silver indium sulfide ($AgInS_2$) can also be used. Quantum dots show very narrow emission bands. Quantum dots of any specific size typically have a light distribution (emission peak) with a full width at half maximum (FWHM) in the range of 30-60 nm. Furthermore the emission color can easily be tuned by adapting the size of the quantum dots. Any type of quantum dot known in the art may be used in the present invention. However, it may be preferred for reasons of environmental safety and concern to use cadmium-free quantum dots or at least quantum dots having a relatively low cadmium content. Cadmium based quantum dots have in general a smaller FWHM compared to cadmium free quantum dots.

In embodiments of the present invention, several types of quantum dots are typically used in combination, and optionally with one or more other inorganic and/or organic phosphor(s). Alternatively, a single type of quantum dot may be used in combination with one or more inorganic and/or organic phosphor(s).

For example, in embodiments of the invention, a plurality of wavelength converting materials, typically quantum dots, selected from among materials 1-16 having emission ranges as specified in Table 1 may be used.

TABLE 1

| Wavelength converting material type | Emission wavelengths (converted) | Color of emitted light |
| --- | --- | --- |
| 1 | 400-440 nm | blue violet (BV) |
| 2 | 440-460 nm | violet blue (VB) |
| 3 | 460-480 nm | blue (B) |
| 4 | 480-490 nm | green blue (GB) |
| 5 | 490-500 nm | blue green (BG) |
| 6 | 500-530 nm | green (G) |
| 7 | 530-560 nm | yellow green (YG) |
| 8 | 560-570 nm | green yellow (GY) |
| 9 | 570-580 nm | yellow |
| 10 | 580-590 nm | orange yellow (OY) |
| 11 | 590-600 nm | yellow orange (YO) |
| 12 | 600-620 nm | orange (O) |
| 13 | 620-640 nm | red orange (RO) |
| 14 | 640-700 nm | orange red (OR) |
| 15 | 700-750 nm | red (R) |
| 16 | 750-800 nm | near infrared (NIR) |

Optionally, all 16 types of materials may be used together, although it is also possible to use less than 16 different types of material. For example, in embodiments of the invention, at least three, and typically at least five different wavelength converting materials selected from materials 1-16 listed in Table 1 may be used. Typically, enough wavelength materials are used to provide a total emission spectrum that yields white light, preferably having a color point on or near the black body line as represented in a CIE chromaticity diagram.

In embodiments of the present invention, the wavelength converting material may be provided directly on a solid state light emitting element, e.g. forming a phosphor-converted LED as shown e.g. in FIG. 3. Alternatively, the wavelength converting material may be provided at a small distance from an solid state light emitting element, sometimes referred to as "vicinity mode" or "vicinity configuration". In yet other embodiments, the wavelength converting materials may be positioned remotely from the solid state light emitting element (also referred to as "remote phosphor" or "remote configuration"), e.g. as shown in any of FIGS. 5a, 6a-b, 7a.

Although the solid state light emitting element described above with reference to the drawings is represented by a blue of UV LED element, it is contemplated that other solid state light emitting elements may be used, including for example LED elements of other colors (for example, violet), organic light emitting diodes (OLEDs), and laser diodes. Solid state light emitting elements are in general inexpensive and have high efficiency and long life-time.

The light (total emission spectrum) emitted by the light emitting arrangements, light sources, spotlights etc., described herein is preferably white light, which may have a color point on the black body line as seen in the CIE chromaticity diagram. Furthermore, the emitted light may have a color rendering index (CRI) of at least 80.

Figure 10:
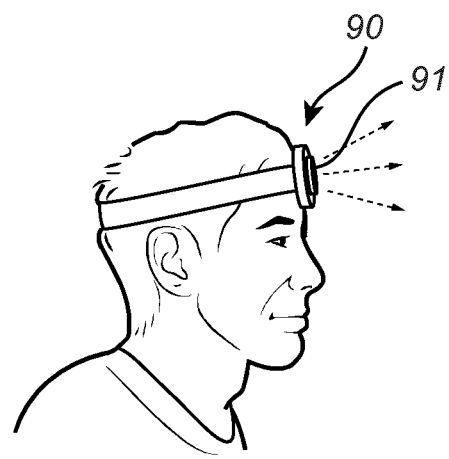
FIG. 10 is a side view illustrating a person wearing a head torch comprising a spotlight according to embodiments of the invention.

According to the present invention, the light emitting arrangement described above is advantageously utilized in a spotlight, especially a spotlight for use as or in a surgical light source. FIG. 10 shows a head torch 90 intended to be worn by a person, e.g. surgical personnel, comprising a spotlight 91 comprising at least one light emitting arrangement as described herein. The head torch typically comprises at least one spotlight mounted on an adjustable member adapted to be worn on the head. Alternatively, a light emitting arrangement as described above may be used in a handheld torch.

Figure 11:
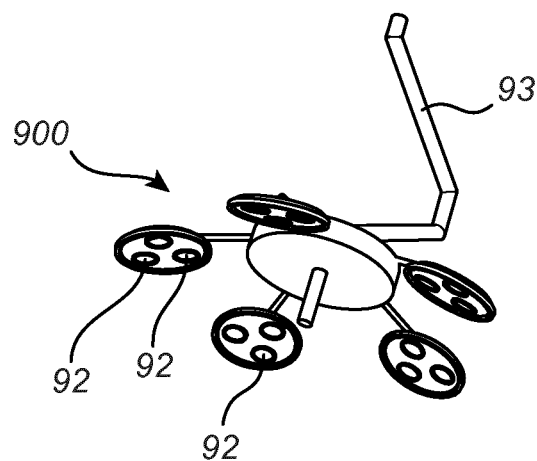
FIG. 11 is a perspective view illustrating a surgical lighting system according to embodiments of the invention.
Figure 11:
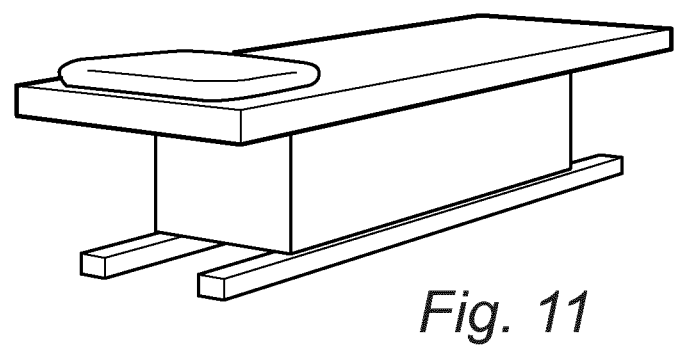

FIG. 11 shows another embodiment of the invention represented by a surgical lighting system 900 comprising a plurality of spotlights 92, here arranged three-by-three in manner conventional for surgical lighting systems. The lighting system is typically adapted to be mounted in the ceiling of a room, e.g. of an operating room as shown in FIG. 10, or on a wall, or on a standing support, e.g. using an adjustable and/or extendible support arm 93.

The above described the light emitting arrangements, light sources and spotlights, etc., may advantageously be used for illuminating objects comprising a fluorescent molecule, in particular a fluorescent molecule which has en emission peak corresponding to the "hole" or "dip" in the emission spectrum of the light emitting arrangement, light source, spotlight etc. as described above. Hence, the light emitting arrangements, light sources and spotlights, etc., may be employed in a method for detecting a fluorescent molecule, comprising the step of illuminating an object comprising the fluorescent molecule using the light source, spotlight etc. according to embodiments of the invention.

In embodiments, the fluorescent molecule may be a biomarker and the object comprising the biomarker may be a biological material. Examples of biological materials include live and dead biological material, such as a biological sample taken from a live or dead organism; cells; tissues; organs; and human and animal subjects, e.g. a patient undergoing or about to undergo medical examination, diagnosis, treatment and/or surgery.

The person skilled in the art realizes that the present invention by no means is limited to the preferred embodiments described above. On the contrary, many modifications and variations are possible within the scope of the appended claims. For example, the light emitting arrangements, light sources, spotlights etc. described herein may be used for detecting fluorescent molecules in environments and contexts other than surgical or medical, such as detecting or enhancing fluorescent signals in research and/or commercial applications within other technical (non-medical) fields, security applications, decorative applications, etc.

Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage.

The invention claimed is:

1. A spotlight configured to produce white light, comprising:
   at least one solid state light emitting element configured to emit primary light; and
   a plurality of wavelength converting materials, configured to convert part of the primary light into secondary light, provided as an array of independent wavelength converting domains,
   wherein different wavelength converting domains comprise wavelength converting materials producing different secondary light emission bands or peaks, each wavelength converting material being configured to convert primary light into a secondary light wavelength range wherein each wavelength converting material is configured to contribute to a total emission spectrum with at least one emission band or peak and wherein a total secondary light emission provided by said wavelength converting materials provides a broad band emission spectrum except for at least one defined narrow wavelength range in which the spotlight produces significantly reduced light emission, and
   wherein the combined emission of light converted by the wavelength converting materials is controllable to form an emission spectrum with significantly reduced light emission in said at least one defined narrow wavelength range,
   said spotlight further comprising a controllable shielding member arranged to shield at least one wavelength converting domain from receiving primary light to reduce emission light of said at least one defined narrow wavelength range,
   wherein said emission spectrum of the combined emission is still perceived as white, and
   wherein said at least one defined narrow wavelength range corresponds to a fluorescent wavelength range of a fluorescent marker to be illuminated by the spot light.

2. The spotlight according to claim 1, comprising a plurality of independently controllable solid state light sources, wherein each wavelength converting domain is arranged to receive light emitted by one of said independently controllable solid state light sources.

3. The spotlight according to claim 1, wherein at least one wavelength converting material comprises at least one type of quantum dots.

4. The spotlight according to claim 1, wherein at least one wavelength converting material comprises one or several types of organic wavelength converting materials.

5. The spotlight according to claim 1, further comprising a light sensor and a control unit operatively connected to the light sensor and to said controllable shielding member or said independently controllable light sources, wherein said control unit is configured to control the emission spectrum of the spotlight.

6. A head torch comprising a spotlight according to claim 1.

7. A handheld torch comprising a spotlight according to claim 1.

8. A surgical lighting system comprising at least one spotlight according to claim 1.

9. A method of detecting a fluorescent molecule, comprising illuminating an object comprising the fluorescent molecule using a spotlight according to claim 1.

10. The method according to claim 9, wherein the fluorescent molecule is a biomarker and the illuminated object is a biological material.

11. A method of operating a spotlight configured to produce white light, the spotlight comprising: at least one solid state light emitting element configured to emit primary light, and a plurality of wavelength converting materials, configured to convert part of the primary light into secondary light, provided as an array of independent wavelength converting domains, wherein different wavelength converting domains comprise wavelength converting materials producing different secondary light emission bands or peaks, each wavelength converting material being configured to convert primary light into a secondary light wavelength range, wherein each wavelength converting material is configured to contribute to a total emission spectrum with at least one emission band or peak and wherein a total secondary light emission provided by said wavelength converting materials provides a broad band emission spectrum except for at least one defined narrow wavelength range in which the spotlight produces significantly reduced light emission, and wherein the combined emission of light converted by the wavelength converting materials is controllable to form an emission spectrum with significantly reduced light emission in said at least one defined narrow wavelength range, said spotlight further comprising a controllable shielding member arranged to shield at least one wavelength converting domain from receiving primary light to reduce emission light of said at least one defined narrow wavelength range, wherein said emission spectrum of the combined emission is still perceived as white, and wherein said at least one defined narrow wavelength range corresponds to a fluorescent wavelength range of a fluorescent marker to be illuminated by the spot light, and a light sensor and a control unit operatively connected to the light sensor and to said controllable shielding member or said independently controllable light sources, wherein said control unit is configured to control the emission spectrum of the spotlight, the method comprising:
   detecting light emitted by an object to be illuminated by the spotlight;
   controlling the operation of the shielding member to reduce emission of light of a wavelength range emitted by the object to be illuminated; and
   illuminating the object with light emitted by the spotlight.

12. A spotlight configured to produce white light, comprising:
   at least one solid state light emitting element configured to emit primary light; and
   a plurality of wavelength converting materials, configured to convert part of the primary light into secondary light, and provided as an array of independent wavelength converting domains,
   wherein different wavelength converting domains comprise wavelength converting materials producing different secondary light emission bands or peaks, each wavelength converting material being configured to convert primary light into a secondary light wavelength range wherein each wavelength converting material is configured to contribute to a total emission spectrum with at least one emission band or peak and the total secondary light emission provided by said wavelength converting materials provides a broad band emission spectrum except for at least one defined narrow wavelength range in which the spotlight produces no light emission, and wherein the combined emission of light converted by the wavelength converting materials is controllable to form an emission spectrum with no light emission in said at least one defined narrow wavelength range, said spotlight further comprising a controllable shielding member arranged to prevent emission light of said at least one defined narrow wavelength range, wherein said emission spectrum of the combined emission is still perceived as white, and wherein said at least one defined narrow wavelength range corresponds to a fluorescent wavelength range of a fluorescent marker to be illuminated by the spot light.

* * * * *